United States Patent [19]
Mackool

[11] Patent Number: 5,810,857
[45] Date of Patent: Sep. 22, 1998

[54] SURGICAL KNIFE FOR CONTROLLED LENGTHENING OF AN INCISION

[76] Inventor: Richard J. Mackool, 31-27 41st St., Astoria, N.Y. 11103

[21] Appl. No.: 509,417

[22] Filed: Jul. 31, 1995

Related U.S. Application Data

[63] Continuation of Ser. No. 104,901, Aug. 12, 1993, abandoned.

[51] Int. Cl.$^6$ ..................................................... A61B 17/32
[52] U.S. Cl. ........................... 606/167; 606/166; 606/172; 30/351; 30/357
[58] Field of Search ..................................... 606/166, 167, 606/172; 30/351, 357, 305

[56] References Cited

U.S. PATENT DOCUMENTS

| | | | |
|---|---|---|---|
| 3,897,629 | 8/1975 | Liedtke | 30/351 X |
| 4,787,146 | 11/1988 | Gaskins | 30/351 X |
| 5,203,865 | 4/1993 | Siepser | 606/166 |
| 5,222,967 | 6/1993 | Casebeer et al. | 606/166 |
| 5,376,099 | 12/1994 | Ellis et al. | 606/166 |

OTHER PUBLICATIONS

Comparison of the Standard Combined (Bidirectional) Radial Keratotomy Technique With the Undercut Technique in Human Donor Eyes, Parks, et al., Journal of Refractive Surgery, vol. 12, Jan./Feb. 1996, pp. 77–84.

Coopervision Publication (2 pages) 1985.

*Primary Examiner*—Michael H. Thaler
*Attorney, Agent, or Firm*—Cobrin Gittes & Samuel

[57] ABSTRACT

A surgical knife has a blade portion including a sharp edge disposed in a first plane and a dull portion offset from the first plane by a selected amount substantially equal to the amount of desired lengthening. When the blade is inserted into a previously-formed incision in tissue and moved in the direction of desired lengthening, the sharp edge cuts the tissue to lengthen the incision until the dull portion abuts against a wall of the incision to prevent further travel of the blade. The dull portion thus acts as a "stop" which prevents further travel of the blade beyond a desired point, enabling controlled lengthening of the incision.

3 Claims, 5 Drawing Sheets

SURGICAL KNIFE FOR CONTROLLED LENGTHENING OF AN INCISION

This is a continuation of application Ser. No. 08/104,901, filed Aug. 12, 1993, now abandoned.

BACKGROUND OF THE INVENTION

This invention relates generally to a surgical instrument for making surgical incisions, and, more particularly, relates to a surgical knife for extending in a controlled manner the length of a surgical incision.

DESCRIPTION OF THE PRIOR ART

Various forms of surgical knives exist. Examples of such devices are set forth in the following United States patents:

| U.S. Pat. No. | Inventor | Date |
| --- | --- | --- |
| 2,649,860 | Royer | Aug. 25, 1953 |
| 3,798,688 | Wasson | Mar. 26, 1974 |
| 4,844,070 | Dee | Jul. 04, 1989 |
| 5,201,747 | Mastel | Apr. 13, 1993 |

U.S. Pat. No. 2,649,860 to Royer discloses a surgical instrument having a concave cutting saddle 15 bounded by rounded surfaces 12 and 16. As stated at col. 2 of Royer, "the purposes of having rounded edges through the major portion of the knife is to avoid injury to important tissues in the hand."

U.S. Pat. No. 3,798,688 to Wasson discloses a surgical scalpel construction having an outer blade end which is pointless to prevent accidental stabbing of the surgeon or assistant during transfer of the scalpel and which may be formed with a concave tip portion having sharp side edges for cutting. See, for example. FIGS. 1 and 4 of Wasson.

U.S. Pat. No. 4,844,070 to Dee discloses a changeable scalpel blade and chuck assembly.

U.S. Pat. No. 5,201,747 to Mastel discloses an ophthalmological surgical instrument having a triple edge tip.

Surgical scalpels typical of the prior art, however, suffer from a number of deficiencies. Most notably, conventional scalpels and surgical knives do not provide for extremely precise extension of the length of a previously made surgical incision. It is common practice in surgery, and particularly in ocular surgery where there is a corneal incision, for the surgeon to make an incision of a predetermined length. Further, it is often necessary, at that time or at a later time, to enlarge the incision by a minuscule amount. This required lengthening of the original incision is typically for a quarter of a millimeter or less, and accuracy is essential. Unintended lengthening of an incision beyond the desired distance can be extremely harmful to the patient, particularly when forming an incision in the cornea.

Because of the extremely short distances involved and the need for accuracy, the lengthening procedure can be very difficult, even for highly skilled surgeons.

SUMMARY OF THE INVENTION

It is accordingly an object of the present invention to provide a surgical knife that enables precise and controlled lengthening of a surgical incision.

It is a further object of the present invention to provide such a knife having a blade configuration that facilitates the lengthening of a previously-formed incision by a predetermined amount.

It is another object of the invention to provide an improved surgical knife that is easily used by a surgeon to extend the length of a previously formed incision by a minuscule amount, on the order of one-quarter of a millimeter or less.

Other general and specific objects of the invention will in part be obvious and will in part appear hereinafter.

The foregoing objects are attained by the present invention, which provides a surgical knife for controlled lengthening of a previously-formed surgical incision.

In accordance with one aspect of the invention, the surgical knife has a blade portion including a sharp edge disposed in a first plane and a dull portion disposed offset from the first plane by a selected amount substantially equal to the amount of desired lengthening. When the blade is inserted into a previously-formed incision in tissue and moved in the direction of desired lengthening, the sharp edge cuts the tissue to lengthen the incision until the dull portion abuts against a wall of the incision to prevent further travel of the blade. The dull portion thus acts as a "stop" which prevents further travel of the blade beyond a desired point.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which.

DESCRIPTION OF ILLUSTRATED EMBODIMENTS

Figure 1A:
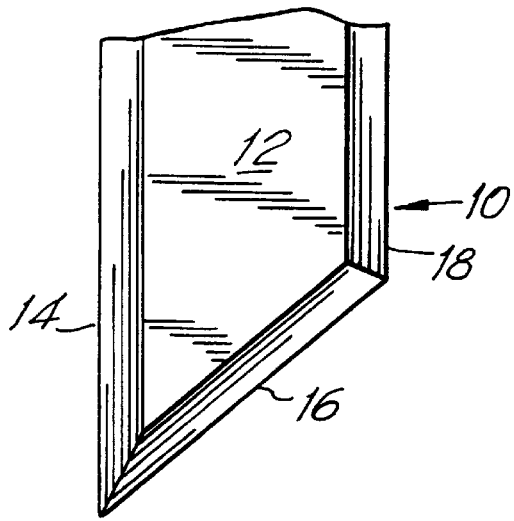
FIG. 1A depicts a side view of a scalpel typical of the prior art.
Figure 1B:
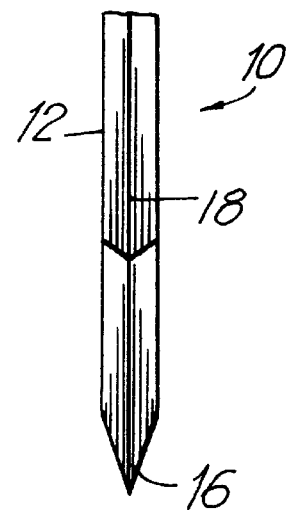
FIG. 1B depicts a front view of a scalpel typical of the prior art.

FIGS. 1A and 1B depict side and front views, respectively, of a scalpel 10 typical of the prior art. The scalpel 10 includes a blade portion 12 having sharp edges 14, 16 and 18 for cutting tissue in a known manner. A scalpel of this type is disclosed in U.S. Pat. No. 5,201,747 to Mastel, the teachings of which are incorporated by reference herein.

While this conventional type of scalpel is useful in ophthalmological surgery, it does not provide for extremely precise extension of the length of a previously made surgical incision. As noted above, it is common practice in corneal surgery for the surgeon to make an incision of a predetermined length, and then, at a later time, to enlarge the incision by a minuscule amount. This required lengthening of the original incision is typically for a quarter of a millimeter or less, and accuracy is essential. Because of the extremely short distances involved and the need for accuracy, the lengthening procedure can be very difficult, even for highly skilled surgeons.

Controlled lengthening of a previously made incision, however, is provided by a scalpel or knife constructed in accordance with the invention, embodiments of which are depicted in FIGS. 2–6. Referring now to FIGS. 2–6, each of the embodiments of the knife 10 includes a blade portion 12 having a tip portion 13 with a distal side and a proximal side. In the embodiment shown in FIG. 2, tip portion 13 includes at least one sharp distal edge portion 14 on the distal side, disposed along a cutting plane, and a "step" or "notch" section N including a dull edge 20 that is offset or set back by a selected distance S from the cutting plane defined by sharp edge 14. By providing a step or notch in the blade as depicted, an incision can be lengthened by a controlled amount equal to the length S of the step. The offset or set-back distance S of the blade determines the amount of controlled lengthening that can be provided by the knife.

As will be seen below, by providing a sharp edge 14 disposed in a first plane and a dull edge 20 disposed in a second plane set back from the first plane by a selected amount S substantially equal to the amount of desired lengthening, when the blade 12 is inserted into a previously-formed incision in tissue and moved edgewise in the direction of desired lengthening, the sharp edge 14 cuts the tissue to lengthen the incision until the dull edge 20 abuts against a wall of the incision to prevent further travel of the blade. The dull edge 20 thus acts as a "stop" which prevents further travel of the blade beyond a desired point.

Figure 2:
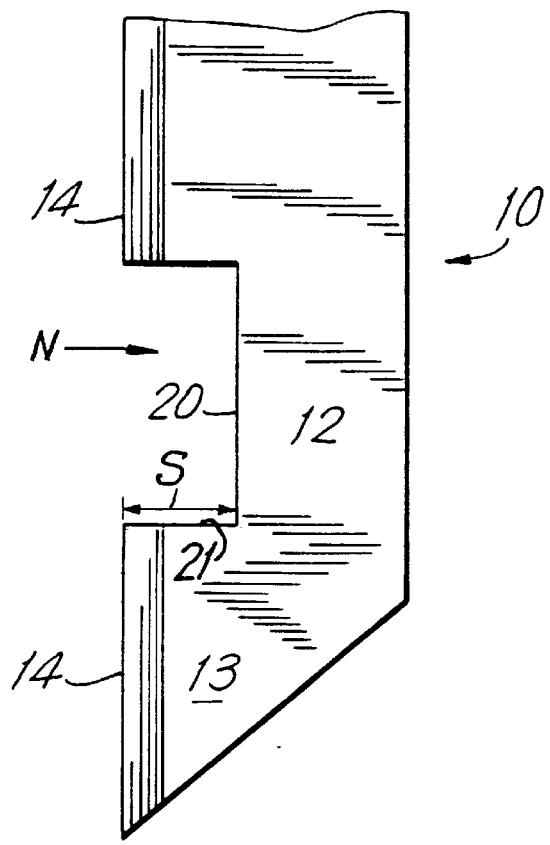
FIG. 2 depicts a side view of one embodiment of a surgical knife constructed in accordance with the invention for controlled lengthening of a surgical incision.
Figure 6:
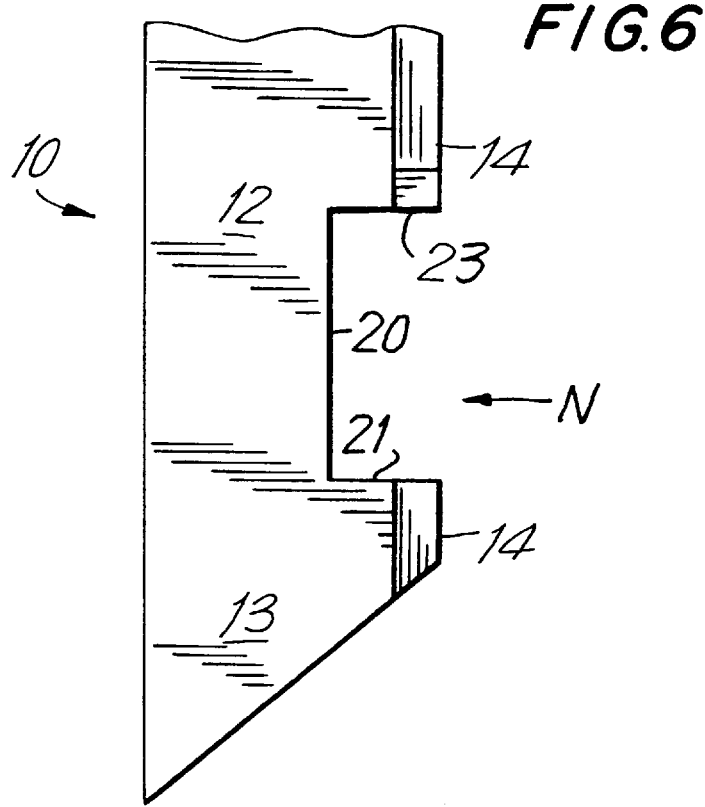
FIG. 6 depicts a fifth embodiment of a surgical knife constructed in accordance with the invention for controlled lengthening of a surgical incision.

In the embodiments depicted in FIGS. 2 and 6, the dull edge 20 forms the "floor" portion of a notched section N which is bounded on two sides by sharp edges 14. FIG. 2 shows a knife adapted for edgewise cutting in a right-to-left direction, while FIG. 6 depicts a configuration adapted for cutting in a left-to-right direction. Moreover, FIG. 2 shows sharp edges 14 and notched section including dull edge 20 disposed on the longer or "point" edge of the blade, while FIG. 6 illustrates the sharp edges and notched section on the shorter edge of the blade. If desired, in FIG. 6 edge 23 may be sharp.

Figure 3:
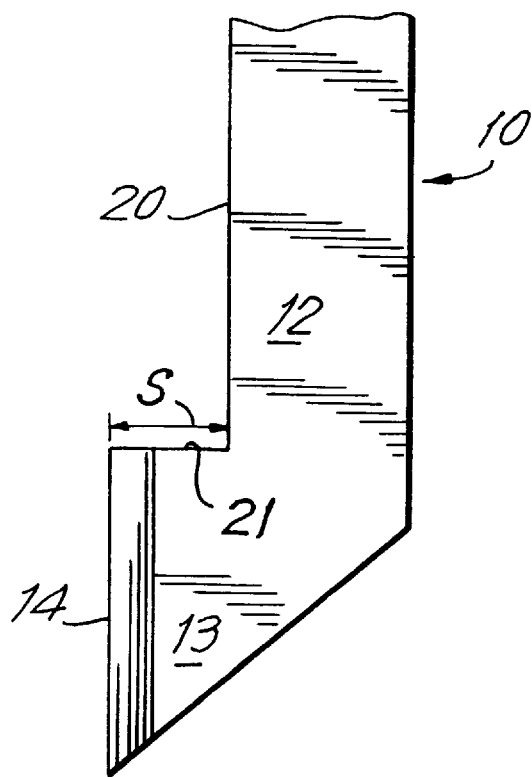
FIG. 3 depicts a second embodiment of a surgical knife constructed in accordance with the invention for controlled lengthening of a surgical incision.

FIG. 3 illustrates an "undercut" blade portion in which the sharp edge portion 14 is terminated by the notch or step portion defined by wall 21. As will be seen below, this configuration is utilized to initially extend the lower portion of an incision.

Figure 4:
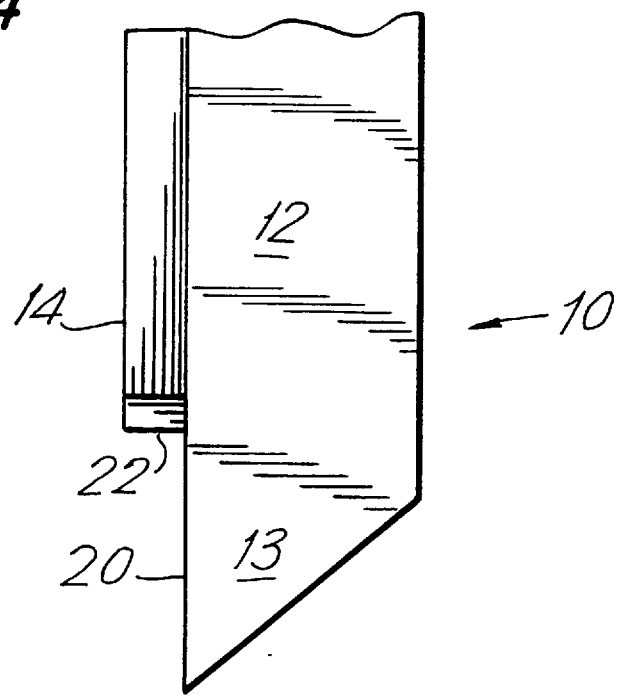
FIG. 4 depicts a third embodiment of a surgical knife constructed in accordance with the invention for controlled lengthening of a surgical incision.
Figure 5:
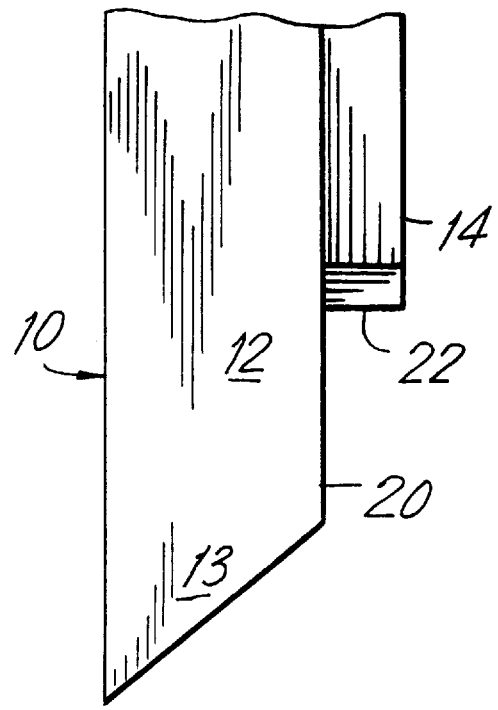
FIG. 5 depicts a fourth embodiment of a surgical knife constructed in accordance with the invention for controlled lengthening of a surgical incision.

FIGS. 4 and 5 illustrate two blade configurations having sharp edges 14 and 22 and a dull edge 20. These blades are utilized by moving the blade in a downward edgewise direction, thereby to lengthen an upper portion of an incision, as will be discussed hereinafter.

Figure 7:
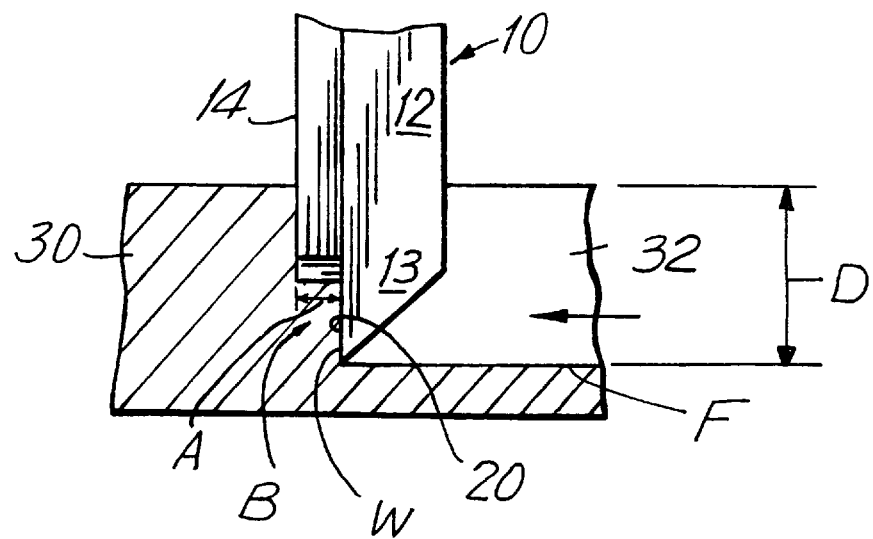
FIG. 7 depicts the use of the embodiment of FIG. 4 to lengthen an incision by cutting an upper layer of tissue by a desired amount.
Figure 8:
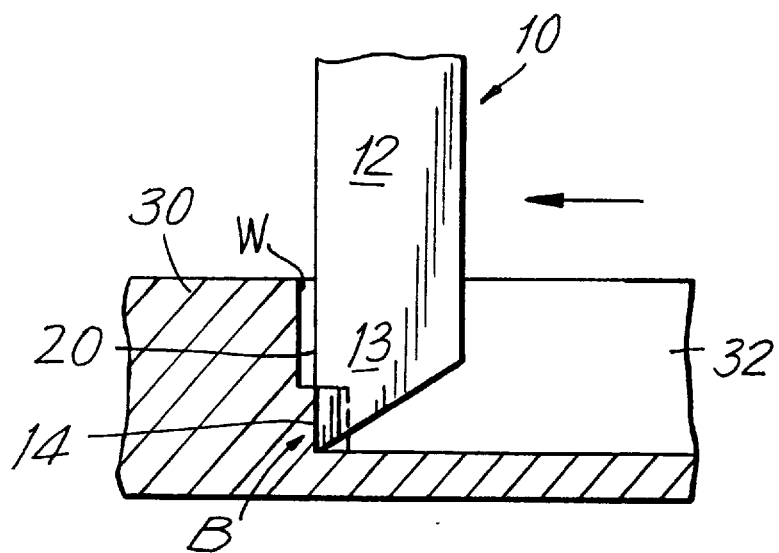
FIG. 8 depicts completion of the lengthening process of FIG. 7 using a conventional scalpel to cut remaining tissue in the lengthened incision region.

An example of this controlled lengthening function is seen in FIGS. 7 and 8. FIG. 7 depicts the use of the knife embodiment 10 of FIG. 4 to lengthen an incision 32 previously made in a cornea 30 by cutting an additional portion A of tissue by a desired amount. FIG. 8 depicts completion of the lengthening process of FIG. 7 using a conventional scalpel to cut remaining tissue in the lengthened incision region.

More particularly, as seen in FIG. 7, the pre-existing incision 32 made in cornea 30 is characterized by a depth D and a distal wall W. In order to lengthen the incision 32 by a desired additional amount A, the surgeon first utilizes knife 10 having a dull tip edge portion 20 and a sharp edge portion 14 set forward from the tip by an amount A. The knife is inserted into the pre-existing incision such that the sharp edge portion 14 abuts against the pre-existing distal wall W of the pre-existing incision. The knife is pushed then forward, so that sharp edge 14 cuts tissue in the additional incision region A, until the dull tip portion of the knife contacts the "wall" W of the pre-existing incision.

Because of the geometry of the knife, particularly the selected offset between sharp edge 14 and dull portion 20, only a selected width of additional tissue A can be cut in the cutting procedure depicted in FIG. 7. This cutting procedure leaves an incision having a "step" region B of additional tissue to be cut. The lengthening process of FIG. 7 is completed by cutting remaining tissue in region B, as shown in FIG. 8, using a conventional scalpel. In particular, the conventional scalpel having sharp edge portion 14 is introduced into the incision and moved from right to left to cut the tissue in region B, thereby completing the lengthening process of FIG. 7.

Figure 9:
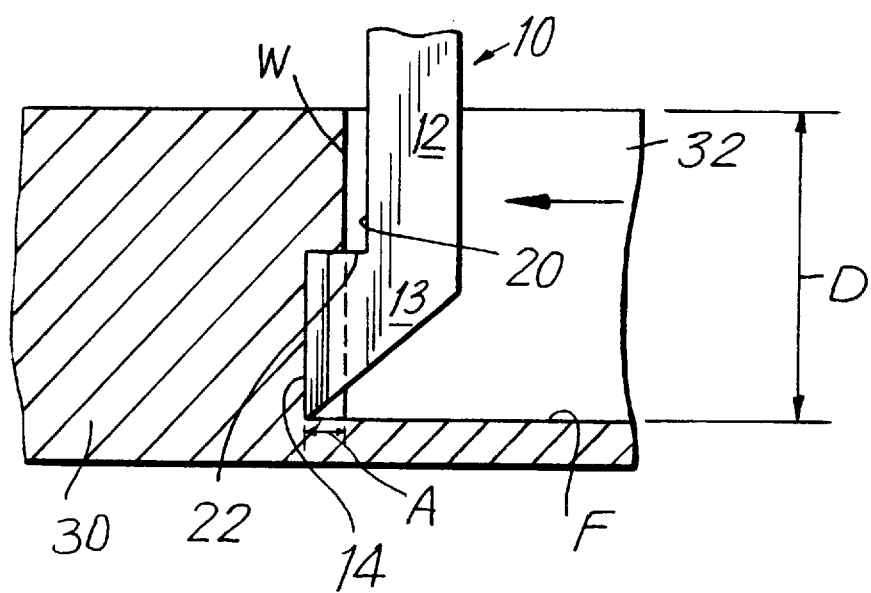
FIG. 9 depicts the use of the embodiment of FIG. 3 to lengthen an incision by cutting a lower layer of tissue by a desired amount.
Figure 10:
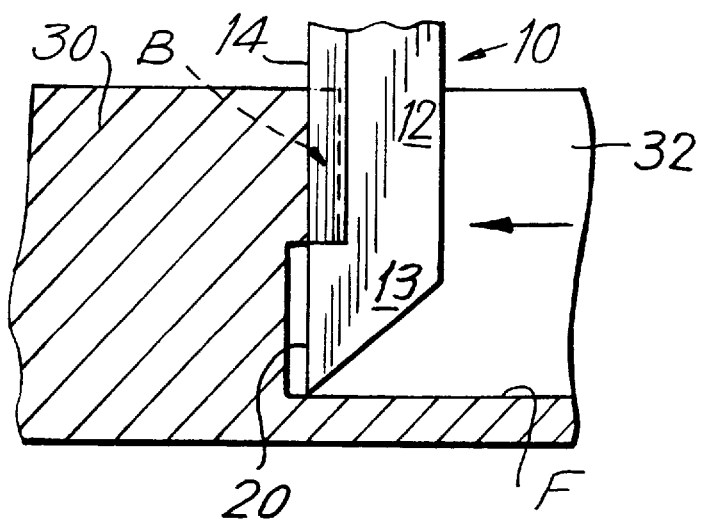
FIG. 10 depicts completion of the lengthening process of FIG. 9 using a conventional scalpel to cut remaining tissue in the lengthened incision region.

FIGS. 9 and 10 depict a similar incision-lengthening process, wherein the knife embodiment of FIG. 3 is used to lengthen an incision by cutting a lower layer of tissue by a desired amount, as shown in FIG. 9, and the lengthening process is completed by using a conventional scalpel to cut remaining tissue in the lengthened incision region (FIG. 10).

As shown in FIG. 9, the pre-existing incision 32 is characterized by a "floor" F, a depth D, and a distal wall W. In accordance with the invention, in order to lengthen the incision 32 by a selected amount A, the surgeon utilizes a knife 10 having a sharp edge 14 at a tip portion 13 of the blade 12, and a dull edge 20 set back from the plane of the sharp edge 14 by a selected distance S equal to the selected amount of lengthening. The knife is introduced into the incision 32 and moved from right to left in the drawing, so that sharp edge 14 cuts tissue in region A and extends the incision, substantially along the same path as the pre-existing incision, until dull portion 20 abuts the wall W of the pre-existing incision.

This cutting operation lengthens the lower portion of pre-existing incision 32 by a selected amount in region A, the selected amount being equal to the offset or set-back S of the blade. As shown in FIG. 10, the initial lengthening step of FIG. 9 leaves a "step" in the incision at upper region B. This step is removed, and the lengthening procedure of FIG. 9 is completed, using a scalpel as shown in FIG. 10. In particular, the knife is introduced into the incision and moved from right to left to cut tissue in region B, thereby completing the lengthening process.

Those skilled in the art will appreciate that the invention can be embodied in other blade configurations. In each of these configurations, the surgical knife will have a blade portion including a sharp edge disposed in a first plane and a dull portion offset from the first plane by a selected amount substantially equal to the amount of desired lengthening. By providing a "step" in the blade as depicted, an incision can be lengthened by a controlled amount equal to the length of the step. When the blade is inserted into a previously-formed incision in tissue and moved in the direction of desired lengthening, the sharp edge cuts the tissue to lengthen the incision until the dull portion abuts against a wall of the incision to prevent further travel of the blade. The dull portion thus acts as a "stop" which prevents further travel of the blade beyond a desired point, enabling controlled lengthening of the incision.

It will thus be seen that the invention efficiently attains the objects set forth above, among those made apparent from the preceding description. In particular, the invention provides a surgical knife that affords precisely controlled lengthening of a previously-formed surgical incision.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense. It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. A surgical knife for facilitating controlled lengthening of previously-formed incision in tissue by a predetermined length comprising:
   a blade including
   a sharp edge disposed along an edge surface of the knife in a first plane for cutting, and
   a dull edge disposed along an edge surface of the knife in a second plane, said second plane being offset from said first plane by a wall having a length of said predetermined length, said dull edge being adapted for abutting a wall portion of the previously-formed incision when the blade is moved said predetermined length substantially along a path defined by the previously-formed incision, said dull edge thereby preventing said sharp edge from travelling farther than said predetermined length, said blade having a bevel terminating at said sharp edge and originating from a location spaced from and between said first and second planes said second plane being offset from said first plane by a second wall, said second wall having a length of said predetermined length such that said second wall and said dull edge are perpendicular to each other, said wall and said second wall facing each other and being separated from each other by a gap, and said wall, said second wall and said dull edge forming a notch in said blade.

2. A surgical knife as in claim 1, wherein said location is disposed in a third plane, said first-mentioned wall including a sharp edge portion that lies between said first plane and said third plane.

3. A surgical knife as in claim 2, wherein a remainder of said wall is free of said sharp edge portion.

* * * * *